(12) United States Patent
Wang et al.

(10) Patent No.: US 7,459,280 B2
(45) Date of Patent: Dec. 2, 2008

(54) METHODS FOR DIAGNOSING AND TREATING KIDNEY CANCER

(75) Inventors: Bruce Wang, Mountain View, CA (US); Matthias Wabl, San Francisco, CA (US)

(73) Assignee: Picobella, LLC, Burlingame, CA (US)

( * ) Notice: Subject to any disclaimer, the term of this patent is extended or adjusted under 35 U.S.C. 154(b) by 28 days.

(21) Appl. No.: 11/363,596

(22) Filed: Feb. 27, 2006

(65) Prior Publication Data
US 2007/0202510 A1   Aug. 30, 2007

(51) Int. Cl.
*G01N 33/574* (2006.01)
(52) U.S. Cl. ........................... 435/7.23; 435/7.1
(58) Field of Classification Search .................. None
See application file for complete search history.

(56) References Cited

U.S. PATENT DOCUMENTS

| | | |
|---|---|---|
| 4,394,448 A | 7/1983 | Szoka et al. |
| 4,442,124 A | 4/1984 | Niklaus |
| 4,595,695 A | 6/1986 | Ladkani et al. |
| 4,798,823 A | 1/1989 | Witzel |
| 4,816,567 A | 3/1989 | Cabilly et al. |
| 4,885,276 A | 12/1989 | Witzel |
| 4,897,355 A | 1/1990 | Eppstein et al. |
| 4,914,188 A | 4/1990 | Dumont et al. |
| 5,122,511 A | 6/1992 | Patchett et al. |
| 5,162,573 A | 11/1992 | Chiesi et al. |
| 5,214,130 A | 5/1993 | Patchett et al. |
| 5,225,539 A | 7/1993 | Winter |
| 5,227,467 A | 7/1993 | Durette et al. |
| 5,236,899 A | 8/1993 | Durette |
| 5,440,023 A | 8/1995 | Cheng et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,585,358 A | 12/1996 | Bialer et al. |
| 5,625,126 A | 4/1997 | Lonberg et al. |
| 5,633,426 A | 5/1997 | Namikawa et al. |
| 5,661,016 A | 8/1997 | Lonberg et al. |
| 5,693,761 A | 12/1997 | Queen et al. |
| 5,693,762 A | 12/1997 | Queen et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 6,180,370 B1 | 1/2001 | Queen et al. |
| 6,268,396 B1 | 7/2001 | Nau et al. |
| 6,313,106 B1 | 11/2001 | Kozak |
| 6,323,365 B1 | 11/2001 | Blaler et al. |
| 6,458,840 B2 | 10/2002 | Nau et al. |
| 6,555,585 B2 | 4/2003 | Shirvan et al. |
| 6,602,684 B1 | 8/2003 | Umana et al. |
| 6,809,077 B2 | 10/2004 | Or et al. |
| 7,141,648 B2 | 11/2006 | Naicker et al. |

OTHER PUBLICATIONS

Tockman et al, Cancer Res., 1992, 52:2711s-2718s.*
Ficarra et al, Lancet Oncol, 2007, 8:554-558.*
Collier et al., "Cancer gene discovery in solid tumours using transposon-based somatic mutagenesis in the mouse", *Nature*, 436:272-276 (2005).
Dupuy et al., "Mammalian mutagenesis using a highly mobile somatic Sleeping Beauty transposon system", *Nature*, 436:221-226 (2005).
Hadjantonakis et al., "mCelsr1 is an evolutionarily conserved seven-pass transmembrane receptor and is expressed during mouse embryonic development", *Mech Dev.*, 78:91-5 (1998).
Hadjantonakis, A. K. et al., "Celsr1, a neural-specific gene encoding an unusual seven-pass transmembrane receptor, maps to mouse chromosome 15 and human chromosome 22qter", *Genomics*, 45:97-104 (1997).
Li, J. et al., "Leukaemia disease genes: large-scale cloning and pathway predictions", *Nat Genet.*, 23:348-53 (1999).
Lovmand, J. et al., "B-Cell lymphoma induction by akv murine leukemia viruses harboring one or both copies of the tandem repeat in the U3 enhancer", *J. Virol.*, 72:5745-56 (1998).
Lund et al., "Genome-wide retroviral insertional tagging of genes involved in cancer in Cdkn2a-deficient mice", *Nat Genet*, 32:160 (2002).
Mikkers et al. "High-throughput retroviral tagging to identify components of specific signaling pathways in cancer", *Nat Genet*, 32:153-159 (2002).
Nusse et al., "Mode of proviral activation of a putative mammary oncogene (int-1) on mouse chromosome 15", *Nature*, 307:131-136 (1984).
Nusse, R., and H. E. Varmus, "Many tumors induced by the mouse mammary tumor virus contain a provirus integrated in the same region of the host genome", *Cell* 31:99-109 (1982).
Sorensen et al., "Sequence tags of a provirus integration sites in DNAs of tumors induced by the murine retrovirus SL3-3", *J Virol*, 70:4063-4070 (1996).
Suzuki, T. et al. "New genes involved in cancer identified by retroviral tagging", *Nat Genet.*, 32:166-74 (2002).
Tissir et al., "Developmental expression profiles in Celsr (Flamingo) genes in the mouse", *Mech Dev.*, 112:157-60 (2002).
Van Lohuizen, M. et al., "Identification of cooperating oncogenes in E mu-myc transgenic mice by provirus tagging", *Cell*, 65:737-52 (1991).
Wu, Q. & Maniatis, T., "Large exons encoding multiple ectodomains are a characteristic feature of protocadherin genes", *Proc Natl Acad Sci U S A*, 97:3124-9 (2000).

* cited by examiner

*Primary Examiner*—Misook Yu
*Assistant Examiner*—Mark Halvorson
(74) *Attorney, Agent, or Firm*—Susan J. Myers Fitch; Peter J. Dehlinger; King & Spalding LLP (57) ABSTRACT

Methods, reagents and kits for diagnosing and treating kidney cancer are disclosed. An immunoassay for detecting kidney cancer is based on the relative change of the CELSR1 protein in urine or blood compared with normal tissue. An immunohistochemical assay for detecting kidney cancer is based on the relative absence of labeled antibody binding to cancerous tissue, compared with normal tissue.

8 Claims, 2 Drawing Sheets

SEQUENCE LISTING

<160> NUMBER OF SEQ ID NOS: 20

<210> SEQ ID NO 1
<211> LENGTH: 61
<212> TYPE: PRT
<213> ORGANISM: Homo sapiens

```
<400> SEQUENCE: 1

Val Arg Leu Val Ala Arg Ser Ala Pro Thr Ala Leu Ser Arg Arg Leu
1               5                   10                  15

Arg Ala Arg Thr His Leu Pro Gly Cys Gly Ala Arg Ala Arg Leu Cys
            20                  25                  30

Gly Thr Gly Ala Arg Leu Cys Gly Ala Leu Cys Phe Pro Val Pro Gly
        35                  40                  45

Gly Cys Ala Ala Ala Gln His Ser Ala Leu Ala Ala Pro
50                  55                  60

<210> SEQ ID NO 2
<211> LENGTH: 202
<212> TYPE: PRT
<213> ORGANISM: Homo sapiens

<400> SEQUENCE: 2

Tyr Gln Val Ala Leu Phe Glu Asn Glu Pro Ala Gly Thr Leu Ile Leu
1               5                   10                  15

Gln Leu His Ala His Tyr Thr Ile Glu Gly Glu Glu Arg Val Ser
            20                  25                  30

Tyr Tyr Met Glu Gly Leu Phe Asp Glu Arg Ser Arg Gly Tyr Phe Arg
        35                  40                  45

Ile Asp Ser Ala Thr Gly Ala Val Ser Thr Asp Ser Val Leu Asp Arg
    50                  55                  60

Glu Thr Lys Glu Thr His Val Leu Arg Val Lys Ala Val Asp Tyr Ser
65                  70                  75                  80

Thr Pro Pro Arg Ser Ala Thr Thr Tyr Ile Thr Val Leu Val Lys Asp
                85                  90                  95

Thr Asn Asp His Ser Pro Val Phe Glu Gln Ser Glu Tyr Arg Glu Arg
            100                 105                 110

Val Arg Glu Asn Leu Glu Val Gly Tyr Glu Val Leu Thr Ile Arg Ala
        115                 120                 125

Ser Asp Arg Asp Ser Pro Ile Asn Ala Asn Leu Arg Tyr Arg Val Leu
    130                 135                 140

Gly Gly Ala Trp Asp Val Phe Gln Leu Asn Glu Ser Ser Gly Val Val
145                 150                 155                 160

Ser Thr Arg Ala Val Leu Asp Arg Glu Glu Ala Ala Glu Tyr Gln Leu
                165                 170                 175

Leu Val Glu Ala Asn Asp Gln Gly Arg Asn Pro Gly Pro Leu Ser Ala
            180                 185                 190

Thr Ala Thr Val Tyr Ile Glu Val Glu Asp
        195                 200

<210> SEQ ID NO 3
<211> LENGTH: 201
<212> TYPE: PRT
<213> ORGANISM: Homo sapiens

<400> SEQUENCE: 3

Glu Tyr Arg Glu Arg Val Arg Glu Asn Leu Val Gly Tyr Glu Val
1               5                   10                  15

Leu Thr Ile Arg Ala Ser Asp Arg Asp Ser Pro Ile Asn Ala Asn Leu
            20                  25                  30

Arg Tyr Arg Val Leu Gly Gly Ala Trp Asp Val Phe Gln Leu Asn Glu
        35                  40                  45
```

-continued

Ser Ser Gly Val Val Ser Thr Arg Ala Val Leu Asp Arg Glu Glu Ala
 50                  55                  60

Ala Glu Tyr Gln Leu Leu Val Glu Ala Asn Asp Gln Gly Arg Asn Pro
 65                  70                  75                  80

Gly Pro Leu Ser Ala Thr Ala Thr Val Tyr Ile Glu Val Glu Asp Glu
                 85                  90                  95

Asn Asp Asn Tyr Pro Gln Phe Ser Glu Gln Asn Tyr Val Val Gln Val
                100                 105                 110

Pro Glu Asp Val Gly Leu Asn Thr Ala Val Leu Arg Val Gln Ala Thr
            115                 120                 125

Asp Arg Asp Gln Gly Gln Asn Ala Ala Ile His Tyr Ser Ile Leu Ser
    130                 135                 140

Gly Asn Val Ala Gly Gln Phe Tyr Leu His Ser Leu Ser Gly Ile Leu
145                 150                 155                 160

Asp Val Ile Asn Pro Leu Asp Phe Glu Asp Val Gln Lys Tyr Ser Leu
                165                 170                 175

Ser Ile Lys Ala Gln Asp Gly Gly Arg Pro Pro Leu Ile Asn Ser Ser
            180                 185                 190

Gly Val Val Ser Val Gln Val Leu Asp
            195                 200

<210> SEQ ID NO 4
<211> LENGTH: 200
<212> TYPE: PRT
<213> ORGANISM: Homo sapiens

<400> SEQUENCE: 4

Tyr Val Val Gln Val Pro Glu Asp Val Gly Leu Asn Thr Ala Val Leu
 1                   5                  10                  15

Arg Val Gln Ala Thr Asp Arg Asp Gln Gly Gln Asn Ala Ala Ile His
                 20                  25                  30

Tyr Ser Ile Leu Ser Gly Asn Val Ala Gly Gln Phe Tyr Leu His Ser
             35                  40                  45

Leu Ser Gly Ile Leu Asp Val Ile Asn Pro Leu Asp Phe Glu Asp Val
 50                  55                  60

Gln Lys Tyr Ser Leu Ser Ile Lys Ala Gln Asp Gly Gly Arg Pro Pro
 65                  70                  75                  80

Leu Ile Asn Ser Ser Gly Val Val Ser Val Gln Val Leu Asp Val Asn
                 85                  90                  95

Asp Asn Glu Pro Ile Phe Val Ser Ser Pro Phe Gln Ala Thr Val Leu
                100                 105                 110

Glu Asn Val Pro Leu Gly Tyr Pro Val Val His Ile Gln Ala Val Asp
            115                 120                 125

Ala Asp Ser Gly Glu Asn Ala Arg Leu His Tyr Arg Leu Val Asp Thr
    130                 135                 140

Ala Ser Thr Phe Leu Gly Gly Ser Ala Gly Pro Lys Asn Pro Ala
145                 150                 155                 160

Pro Thr Pro Asp Phe Pro Phe Gln Ile His Asn Ser Ser Gly Trp Ile
                165                 170                 175

Thr Val Cys Ala Glu Leu Asp Arg Glu Glu Val Glu His Tyr Ser Phe
            180                 185                 190

Gly Val Glu Ala Val Asp His Gly
            195                 200

```
<210> SEQ ID NO 5
<211> LENGTH: 213
<212> TYPE: PRT
<213> ORGANISM: Homo sapiens

<400> SEQUENCE: 5

Pro Phe Gln Ala Thr Val Leu Glu Asn Val Pro Leu Gly Tyr Pro Val
1               5                   10                  15

Val His Ile Gln Ala Val Asp Ala Asp Ser Gly Glu Asn Ala Arg Leu
            20                  25                  30

His Tyr Arg Leu Val Asp Thr Ala Ser Thr Phe Leu Gly Gly Gly Ser
        35                  40                  45

Ala Gly Pro Lys Asn Pro Ala Pro Thr Pro Asp Phe Pro Phe Gln Ile
    50                  55                  60

His Asn Ser Ser Gly Trp Ile Thr Val Cys Ala Glu Leu Asp Arg Glu
65                  70                  75                  80

Glu Val Glu His Tyr Ser Phe Gly Val Glu Ala Val Asp His Gly Ser
                85                  90                  95

Pro Pro Met Ser Ser Ser Thr Ser Val Ser Ile Thr Val Leu Asp Val
            100                 105                 110

Asn Asp Asn Asp Pro Val Phe Thr Gln Pro Thr Tyr Glu Leu Arg Leu
        115                 120                 125

Asn Glu Asp Ala Ala Val Gly Ser Ser Val Leu Thr Leu Gln Ala Arg
    130                 135                 140

Asp Arg Asp Ala Asn Ser Val Ile Thr Tyr Gln Leu Thr Gly Gly Asn
145                 150                 155                 160

Thr Arg Asn Arg Phe Ala Leu Ser Ser Gln Arg Gly Gly Gly Leu Ile
                165                 170                 175

Thr Leu Ala Leu Pro Leu Asp Tyr Lys Gln Glu Gln Gln Tyr Val Leu
            180                 185                 190

Ala Val Thr Ala Ser Asp Gly Thr Arg Ser His Thr Ala His Val Leu
        195                 200                 205

Ile Asn Val Thr Asp
    210

<210> SEQ ID NO 6
<211> LENGTH: 194
<212> TYPE: PRT
<213> ORGANISM: Homo sapiens

<400> SEQUENCE: 6

Thr Tyr Glu Leu Arg Leu Asn Glu Asp Ala Ala Val Gly Ser Ser Val
1               5                   10                  15

Leu Thr Leu Gln Ala Arg Asp Arg Asp Ala Asn Ser Val Ile Thr Tyr
            20                  25                  30

Gln Leu Thr Gly Gly Asn Thr Arg Asn Arg Phe Ala Leu Ser Ser Gln
        35                  40                  45

Arg Gly Gly Gly Leu Ile Thr Leu Ala Leu Pro Leu Asp Tyr Lys Gln
    50                  55                  60

Glu Gln Gln Tyr Val Leu Ala Val Thr Ala Ser Asp Gly Thr Arg Ser
65                  70                  75                  80

His Thr Ala His Val Leu Ile Asn Val Thr Asp Ala Asn Thr His Arg
                85                  90                  95

Pro Val Phe Gln Ser Ser His Tyr Thr Val Ser Val Ser Glu Asp Arg
            100                 105                 110
```

```
Pro Val Gly Thr Ser Ile Ala Thr Leu Ser Ala Asn Asp Glu Asp Thr
            115                 120                 125

Gly Glu Asn Ala Arg Ile Thr Tyr Val Ile Gln Asp Pro Val Pro Gln
        130                 135                 140

Phe Arg Ile Asp Pro Asp Ser Gly Thr Met Tyr Thr Met Met Glu Leu
145                 150                 155                 160

Asp Tyr Glu Asn Gln Val Ala Tyr Thr Leu Thr Ile Met Ala Gln Asp
                165                 170                 175

Asn Gly Ile Pro Gln Lys Ser Asp Thr Thr Thr Leu Glu Ile Leu Ile
            180                 185                 190

Leu Asp

<210> SEQ ID NO 7
<211> LENGTH: 199
<212> TYPE: PRT
<213> ORGANISM: Homo sapiens

<400> SEQUENCE: 7

His Tyr Thr Val Ser Val Ser Glu Asp Arg Pro Val Gly Thr Ser Ile
1               5                   10                  15

Ala Thr Leu Ser Ala Asn Asp Glu Asp Thr Gly Glu Asn Ala Arg Ile
            20                  25                  30

Thr Tyr Val Ile Gln Asp Pro Val Pro Gln Phe Arg Ile Asp Pro Asp
        35                  40                  45

Ser Gly Thr Met Tyr Thr Met Met Glu Leu Asp Tyr Glu Asn Gln Val
    50                  55                  60

Ala Tyr Thr Leu Thr Ile Met Ala Gln Asp Asn Gly Ile Pro Gln Lys
65                  70                  75                  80

Ser Asp Thr Thr Thr Leu Glu Ile Leu Ile Leu Asp Ala Asn Asp Asn
                85                  90                  95

Ala Pro Gln Phe Leu Trp Asp Phe Tyr Gln Gly Ser Ile Phe Glu Asp
            100                 105                 110

Ala Pro Pro Ser Thr Ser Ile Leu Gln Val Ser Ala Thr Asp Arg Asp
            115                 120                 125

Ser Gly Pro Asn Gly Arg Leu Leu Tyr Thr Phe Gln Gly Gly Asp Asp
        130                 135                 140

Gly Asp Gly Asp Phe Tyr Ile Glu Pro Thr Ser Gly Val Ile Arg Thr
145                 150                 155                 160

Gln Arg Arg Leu Asp Arg Glu Asn Val Ala Val Tyr Asn Leu Trp Ala
                165                 170                 175

Leu Ala Val Asp Arg Gly Ser Pro Thr Pro Leu Ser Ala Ser Val Glu
            180                 185                 190

Ile Gln Val Thr Ile Leu Asp
        195

<210> SEQ ID NO 8
<211> LENGTH: 198
<212> TYPE: PRT
<213> ORGANISM: Homo sapiens

<400> SEQUENCE: 8

Phe Tyr Gln Gly Ser Ile Phe Glu Asp Ala Pro Pro Ser Thr Ser Ile
1               5                   10                  15

Leu Gln Val Ser Ala Thr Asp Arg Asp Ser Gly Pro Asn Gly Arg Leu
            20                  25                  30
```

Leu Tyr Thr Phe Gln Gly Gly Asp Gly Asp Gly Asp Phe Tyr Ile
            35                  40                  45

Glu Pro Thr Ser Gly Val Ile Arg Thr Gln Arg Arg Leu Asp Arg Glu
 50                  55                  60

Asn Val Ala Val Tyr Asn Leu Trp Ala Leu Ala Val Asp Arg Gly Ser
 65                  70                  75                  80

Pro Thr Pro Leu Ser Ala Ser Val Glu Ile Gln Val Thr Ile Leu Asp
                 85                  90                  95

Ile Asn Asp Asn Ala Pro Met Phe Glu Lys Asp Glu Leu Glu Leu Phe
                100                 105                 110

Val Glu Glu Asn Asn Pro Val Gly Ser Val Val Ala Lys Ile Arg Ala
                115                 120                 125

Asn Asp Pro Asp Glu Gly Pro Asn Ala Gln Ile Met Tyr Gln Ile Val
            130                 135                 140

Glu Gly Asp Met Arg His Phe Phe Gln Leu Asp Leu Leu Asn Gly Asp
145                 150                 155                 160

Leu Arg Ala Met Val Glu Leu Asp Phe Glu Val Arg Arg Glu Tyr Val
                165                 170                 175

Leu Val Val Gln Ala Thr Ser Ala Pro Leu Val Ser Arg Ala Thr Val
                180                 185                 190

His Ile Leu Leu Val Asp
            195

<210> SEQ ID NO 9
<211> LENGTH: 195
<212> TYPE: PRT
<213> ORGANISM: Homo sapiens

<400> SEQUENCE: 9

Glu Leu Glu Leu Phe Val Glu Glu Asn Asn Pro Val Gly Ser Val Val
 1               5                  10                  15

Ala Lys Ile Arg Ala Asn Asp Pro Asp Glu Gly Pro Asn Ala Gln Ile
                 20                  25                  30

Met Tyr Gln Ile Val Glu Gly Asp Met Arg His Phe Phe Gln Leu Asp
             35                  40                  45

Leu Leu Asn Gly Asp Leu Arg Ala Met Val Glu Leu Asp Phe Glu Val
 50                  55                  60

Arg Arg Glu Tyr Val Leu Val Val Gln Ala Thr Ser Ala Pro Leu Val
 65                  70                  75                  80

Ser Arg Ala Thr Val His Ile Leu Leu Val Asp Gln Asn Asp Asn Pro
                 85                  90                  95

Pro Val Leu Pro Asp Phe Gln Ile Leu Phe Asn Asn Tyr Val Thr Asn
                100                 105                 110

Lys Ser Asn Ser Phe Pro Thr Gly Val Ile Gly Cys Ile Pro Ala His
            115                 120                 125

Asp Pro Asp Val Ser Asp Ser Leu Asn Tyr Thr Phe Val Gln Gly Asn
            130                 135                 140

Glu Leu Arg Leu Leu Leu Leu Asp Pro Ala Thr Gly Glu Leu Gln Leu
145                 150                 155                 160

Ser Arg Asp Leu Asp Asn Asn Arg Pro Leu Glu Ala Leu Met Glu Val
                165                 170                 175

Ser Val Ser Asp Gly Ile His Ser Val Thr Ala Phe Cys Thr Leu Arg
            180                 185                 190

Val Thr Ile
        195

<210> SEQ ID NO 10
<211> LENGTH: 37
<212> TYPE: PRT
<213> ORGANISM: Homo sapiens

<400> SEQUENCE: 10

Glu Ile Asp Leu Cys Tyr Ser Asp Pro Cys Gly Ala Asn Gly Arg Cys
1               5                   10                  15

Arg Ser Arg Glu Gly Gly Tyr Thr Cys Glu Cys Phe Glu Asp Phe Thr
            20                  25                  30

Gly Glu His Cys Glu
        35

<210> SEQ ID NO 11
<211> LENGTH: 35
<212> TYPE: PRT
<213> ORGANISM: Homo sapiens

<400> SEQUENCE: 11

Cys Ala Asn Gly Val Cys Lys Asn Gly Gly Thr Cys Val Asn Leu Leu
1               5                   10                  15

Ile Gly Gly Phe His Cys Val Cys Pro Pro Gly Glu Tyr Glu Arg Pro
            20                  25                  30

Tyr Cys Glu
        35

<210> SEQ ID NO 12
<211> LENGTH: 184
<212> TYPE: PRT
<213> ORGANISM: Homo sapiens

<400> SEQUENCE: 12

Thr Arg Ser Phe Pro Pro Gln Ser Phe Val Thr Phe Arg Gly Leu Arg
1               5                   10                  15

Gln Arg Phe His Phe Thr Ile Ser Leu Thr Phe Ala Thr Gln Glu Arg
            20                  25                  30

Asn Gly Leu Leu Leu Tyr Asn Gly Arg Phe Asn Glu Lys His Asp Phe
        35                  40                  45

Ile Ala Leu Glu Ile Val Asp Glu Gln Val Gln Leu Thr Phe Ser Ala
    50                  55                  60

Gly Glu Thr Thr Thr Thr Val Ala Pro Lys Val Pro Ser Gly Val Ser
65                  70                  75                  80

Asp Gly Arg Trp His Ser Val Gln Val Gln Tyr Tyr Asn Lys Pro Asn
                85                  90                  95

Ile Gly His Leu Gly Leu Pro His Gly Pro Ser Gly Glu Lys Met Ala
            100                 105                 110

Val Val Thr Val Asp Asp Cys Asp Thr Thr Met Ala Val Arg Phe Gly
        115                 120                 125

Lys Asp Ile Gly Asn Tyr Ser Cys Ala Ala Gln Gly Thr Gln Thr Gly
    130                 135                 140

Ser Lys Lys Ser Leu Asp Leu Thr Gly Pro Leu Leu Leu Gly Gly Val
145                 150                 155                 160

Pro Asn Leu Pro Glu Asp Phe Pro Val His Asn Arg Gln Phe Val Gly
                165                 170                 175

Cys Met Arg Asn Leu Ser Val Asp
            180

<210> SEQ ID NO 13
<211> LENGTH: 35
<212> TYPE: PRT
<213> ORGANISM: Homo sapiens

<400> SEQUENCE: 13

Asn Phe Cys Asp Gly Arg Arg Cys Gln Asn Gly Gly Thr Cys Val Asn
1               5                   10                  15

Arg Trp Asn Met Tyr Leu Cys Glu Cys Pro Leu Arg Phe Gly Gly Lys
            20                  25                  30

Asn Cys Glu
        35

<210> SEQ ID NO 14
<211> LENGTH: 153
<212> TYPE: PRT
<213> ORGANISM: Homo sapiens

<400> SEQUENCE: 14

Phe Ser Gly Glu Ser Val Val Ser Trp Ser Asp Leu Asn Ile Ile Ile
1               5                   10                  15

Ser Val Pro Trp Tyr Leu Gly Leu Met Phe Arg Thr Arg Lys Glu Asp
            20                  25                  30

Ser Val Leu Met Glu Ala Thr Ser Gly Gly Pro Thr Ser Phe Arg Leu
        35                  40                  45

Gln Ile Leu Asn Asn Tyr Leu Gln Phe Glu Val Ser His Gly Pro Ser
    50                  55                  60

Asp Val Glu Ser Val Met Leu Ser Gly Leu Arg Val Thr Asp Gly Glu
65                  70                  75                  80

Trp His His Leu Leu Ile Glu Leu Lys Asn Val Lys Glu Asp Ser Glu
                85                  90                  95

Met Lys His Leu Val Thr Met Thr Leu Asp Tyr Gly Met Asp Gln Asn
            100                 105                 110

Lys Ala Asp Ile Gly Gly Met Leu Pro Gly Leu Thr Val Arg Ser Val
        115                 120                 125

Val Val Gly Gly Ala Ser Glu Asp Lys Val Ser Val Arg Arg Gly Phe
    130                 135                 140

Arg Gly Cys Met Gln Gly Val Arg Met
145                 150

<210> SEQ ID NO 15
<211> LENGTH: 38
<212> TYPE: PRT
<213> ORGANISM: Homo sapiens

<400> SEQUENCE: 15

Asp Val Asp Asp Pro Cys Thr Ser Ser Pro Cys Pro Pro Asn Ser Arg
1               5                   10                  15

Cys His Asp Ala Trp Glu Asp Tyr Ser Cys Val Cys Asp Lys Gly Tyr
            20                  25                  30

Leu Gly Ile Asn Cys Val
        35

<210> SEQ ID NO 16
<211> LENGTH: 39
<212> TYPE: PRT
<213> ORGANISM: Homo sapiens

```
<400> SEQUENCE: 16

Val Asp Ala Cys His Leu Asn Pro Cys Glu Asn Met Gly Ala Cys Val
1               5                   10                  15

Arg Ser Pro Gly Ser Pro Gln Gly Tyr Val Cys Glu Cys Gly Pro Ser
            20                  25                  30

His Tyr Gly Pro Tyr Cys Glu
        35

<210> SEQ ID NO 17
<211> LENGTH: 39
<212> TYPE: PRT
<213> ORGANISM: Homo sapiens

<400> SEQUENCE: 17

Pro Cys Asp Cys Phe Pro His Gly Ser His Ser Arg Thr Cys Asp Met
1               5                   10                  15

Ala Thr Gly Gln Cys Ala Cys Lys Pro Gly Val Ile Gly Arg Gln Cys
            20                  25                  30

Asn Arg Cys Asp Asn Pro Phe
        35

<210> SEQ ID NO 18
<211> LENGTH: 62
<212> TYPE: PRT
<213> ORGANISM: Homo sapiens

<400> SEQUENCE: 18

Tyr Asn Gly Cys Pro Lys Ala Phe Glu Ala Gly Ile Trp Trp Pro Gln
1               5                   10                  15

Thr Lys Phe Gly Gln Pro Ala Ala Val Pro Cys Pro Lys Gly Ser Val
            20                  25                  30

Gly Asn Ala Val Arg His Cys Ser Gly Glu Lys Gly Trp Leu Pro Pro
        35                  40                  45

Glu Leu Phe Asn Cys Thr Thr Ile Ser Phe Val Asp Leu Arg
    50                  55                  60

<210> SEQ ID NO 19
<211> LENGTH: 54
<212> TYPE: PRT
<213> ORGANISM: Homo sapiens

<400> SEQUENCE: 19

Thr Lys Pro Val Cys Val Phe Trp Asn His Ser Leu Ala Val Gly Gly
1               5                   10                  15

Thr Gly Gly Trp Ser Ala Arg Gly Cys Glu Leu Leu Ser Arg Asn Arg
            20                  25                  30

Thr His Val Ala Cys Gln Cys Ser His Thr Ala Ser Phe Ala Val Leu
        35                  40                  45

Met Asp Ile Ser Arg Arg
    50

<210> SEQ ID NO 20
<211> LENGTH: 244
<212> TYPE: PRT
<213> ORGANISM: Homo sapiens
```

-continued

```
<400> SEQUENCE: 20

Val Leu Pro Leu Lys Ile Val Thr Tyr Ala Ala Val Ser Leu Ser Leu
1               5                   10                  15

Ala Ala Leu Leu Val Ala Phe Val Leu Leu Ser Leu Val Arg Met Leu
            20                  25                  30

Arg Ser Asn Leu His Ser Ile His Lys His Leu Ala Val Ala Leu Phe
            35                  40                  45

Leu Ser Gln Leu Val Phe Val Ile Gly Ile Asn Gln Thr Glu Asn Pro
        50                  55                  60

Phe Leu Cys Thr Val Val Ala Ile Leu Leu His Tyr Ile Tyr Met Ser
65                  70                  75                  80

Thr Phe Ala Trp Thr Leu Val Glu Ser Leu His Val Tyr Arg Met Leu
                85                  90                  95

Thr Glu Val Arg Asn Ile Asp Thr Gly Pro Met Arg Phe Tyr Tyr Val
            100                 105                 110

Val Gly Trp Gly Ile Pro Ala Ile Val Thr Gly Leu Ala Val Gly Leu
            115                 120                 125

Asp Pro Gln Gly Tyr Gly Asn Pro Asp Phe Cys Trp Leu Ser Leu Gln
130                 135                 140

Asp Thr Leu Ile Trp Ser Phe Ala Gly Pro Ile Gly Ala Val Ile Ile
145                 150                 155                 160

Ile Asn Thr Val Thr Ser Val Leu Ser Ala Lys Val Ser Cys Gln Arg
                165                 170                 175

Lys His His Tyr Tyr Gly Lys Lys Gly Ile Val Ser Leu Leu Arg Thr
            180                 185                 190

Ala Phe Leu Leu Leu Leu Ile Ser Ala Thr Trp Leu Leu Gly Leu
            195                 200                 205

Leu Ala Val Asn Arg Asp Ala Leu Ser Phe His Tyr Leu Phe Ala Ile
        210                 215                 220

Phe Ser Gly Leu Gln Gly Pro Phe Val Leu Leu Phe His Cys Val Leu
225                 230                 235                 240

Asn Gln Glu Val
```

METHODS FOR DIAGNOSING AND TREATING KIDNEY CANCER

FIELD OF THE INVENTION

This invention relates generally to methods for diagnosing and treating kidney cancer.

REFERENCES

The following references are cited below in support of the background of the invention or methods employed in practicing the invention.
1. Wu, Q. & Maniatis, T. Large exons encoding multiple ectodomains are a characteristic feature of protocadherin genes. Proc Natl Acad Sci USA 97, 3124-9 (2000).
2. Hadjantonakis, A. K. et al. Celsr1, a neural-specific gene encoding an unusual seven-pass transmembrane receptor, maps to mouse chromosome 15 and human chromosome 22qter. Genomics 45, 97-104 (1997).
3. Hadjantonakis, A. K., Formstone, C. J. & Little, P. F. mCelsr1 is an evolutionarily conserved seven-pass transmembrane receptor and is expressed during mouse embryonic development. Mech Dev 78, 91-5 (1998).
4. Tissir, F., De-Backer, O., Goffinet, A. M. & Lambert de Rouvroit, C. Developmental expression profiles of Celsr (Flamingo) genes in the mouse. Mech Dev 112, 157-60 (2002).
5. Nusse, R., van Ooyen, A., Cox, D., Fung, Y. K. & Varmus, H. Mode of proviral activation of a putative mammary oncogene (int-1) on mouse chromosome 15. Nature 307, 131-6 (1984).
6. Nusse, R. & Varmus, H. E. Many tumors induced by the mouse mammary tumor virus contain a provirus integrated in the same region of the host genome. Cell 31, 99-109 (1982).
7. Sorensen, A. B., Duch, M., Amtoft, H. W., Jorgensen, P. & Pedersen, F. S. Sequence tags of provirus integration sites in DNAs of tumors induced by the murine retrovirus SL3-3. J Virol 70, 4063-70 (1996).
8. Lund, A. H. et al. Genome-wide retroviral insertional tagging of genes involved in cancer in Cdkn2a-deficient mice. Nat Genet 32, 160-5 (2002).
9. Mikkers, H. et al. High-throughput retroviral tagging to identify components of specific signaling pathways in cancer. Nat Genet 32, 153-9 (2002).
10. Collier, L. S., Carlson, C. M., Ravimohan, S., Dupuy, A. J. & Largaespada, D. A. Cancer gene discovery in solid tumours using transposon-based somatic mutagenesis in the mouse. Nature 436, 272-6 (2005).
11. Dupuy, A. J., Akagi, K., Largaespada, D. A., Copeland, N. G. & Jenkins, N. A. Mammalian mutagenesis using a highly mobile somatic Sleeping Beauty transposon system. Nature 436, 221-6 (2005).
12. Suzuki, T. et al. New genes involved in cancer identified by retroviral tagging. Nat Genet 32, 166-74 (2002).
13. Li, J. et al. Leukaemia disease genes: large-scale cloning and pathway predictions. Nat Genet 23, 348-53 (1999).
14. Lovmand, J. et al. B-Cell lymphoma induction by akv murine leukemia viruses harboring one or both copies of the tandem repeat in the U3 enhancer. J Virol 72, 5745-56 (1998).
15. van Lohuizen, M. et al. Identification of cooperating oncogenes in E mu-myc transgenic mice by provirus tagging. Cell 65, 737-52 (1991).

BACKGROUND OF THE INVENTION

Cancer is caused by genetic aberrations, i.e., mutations. In mutant cells the normal balance between the factors that promote and restrain growth is disrupted, and as a result, these mutant cells proliferate continuously—the hallmark of tumor cells. Mutations can arise spontaneously or by external factors such as chemical mutagens, radiation, or viral integration, which inserts extra-genomic DNA that may or may not contain an oncogene. A cellular gene can be modified by point mutation, insertion and frame shift (including truncation), (functional) deletion (including silencing), or translocation, which sometimes can result in gene fusion. In this way protooncogenes become oncogenes, which promote proliferation, and tumor suppressor genes become inactivated, also inducing tumor growth. Any combination of the above-mentioned changes in DNA can contribute to tumor formation. There are two ways by which mutations result in transformation: the expression level of the genes is changed, or their function is altered. The consequences of these changes may or may not be held in check by the immune system (immune surveillance).

Heretofore, there has been no demonstrated link between changes in CELSR1 levels and kidney cancer. Such a link could have a number of important diagnostic and therapeutic applications. In accordance with the present invention, it has now been discovered that (i) CELSR1 levels change, e.g., drop significantly in kidney cancer cells, and (ii) this change can be measured the blood-fluid and urine sample of patients.

SUMMARY OF THE INVENTION

The invention includes, in one aspect, a histological method for examining human kidney tissue for the presence and extent of kidney cancer. This method involves the steps of staining the kidney tissue with an antibody specific against a selected domain or epitope of CELSR1 and labeled with a detectable marker, to attach the marker to the surface of tissue cells having surface bound CELSR1 protein with that epitope or domain, and determining, based on a reduced distribution and extent of detectable marker with respect to the distribution and extent of marker in normal kidney cells, the presence and extent of kidney cancer in the tissue.

In various embodiments, the antibody may be specific against an epitope contained within SEQ ID NO:1, (i) a cadherin domain, such as contained within a sequence identified by SEQ ID NOS: 2-9, (ii) an EGF_CA domain, such as contained within a sequence identified by SEQ ID NOS: 10, 11, 13, 15, and 16, (iii) a LamG domain, such as contained within a sequence identified by SEQ ID NOS: 12 and 14, (iv) an EGF_Lam domain such as contained within the sequence identified by SEQ ID NO: 17, and (v) other domains, such as contained within sequences identified by SEQ ID MOS: 18-20.

In another aspect, the invention includes an antibody that is specific against an epitope contained with amino acid residues 90-150 of human CELSR1, and defined by SEQ ID NO:1. The antibody may be labeled with a detectable marker suitable for immuno-histochemical detection of cancerous kidney or neuronal tissue, based on the relative absence of histochemical staining of the tissue compared with normal kidney or neuronal issue, respectively.

Also disclosed is a method for identifying genetic mutations associated with an increased risk of kidney cancer. The method involves (a) extracting genomic DNA from cells from cancerous kidney tissue from human patients, (b) for the DNA extracted from cells from each tissue, comparing the sequence of the DNA in a selected region of the CELSR1 gene and its 5'-UTR and 3'-UTR, with a homologous region of DNA from cells from normal, wildtype human kidney tissue, and (c), by this comparing, identifying one or more mutations in said regions associated with an increased risk kidney cancer. The selected region of the gene from at least one of (i) a plurality of exons 1 to 35 of the CELSR1 on chromosome interval 22q13.3, including adjacent splice site acceptor and donor sequences of the exons, (ii) a 5' UTR region within 10 kB or less of exon 1 of the gene, and (iii) a 3'-UTR region within 10 kB or less of exon 35. One exemplary region is a 5' UTR region within 10 kB or less of exon 1 of the CELSR1 gene.

The method may be in constructing a gene chip designed for genetic screening for risk of kidney cancer. For each mutation identified in step (c), a gene fragment capable binding selectively to genomic DNA fragments carrying that mutation, but not to corresponding wildtype DNA fragments is produced, and the different-sequence fragments are attached at known positions on a gene-chip substrate.

In still another aspect, there is provided a method of screening for kidney cancer in a human subject, or staging treatment of kidney cancer in a subject, by reacting a body-fluid sample from the subject with an antibody specific against a selected domain or epitope of CELSR1, and determining from the presence and/or amount of immunoassay product, whether the subject has a reduced level of CELSR1 protein lacking the specific domain or epitope, when compared with a normal range of CELSR1 in human samples, as an indicator of kidney cancer. The body-fluid sample may be urine, and the assayed level of CELSR1 indicative of kidney cancer may be a level less than about 0.1 ng/ml.

The method may be carried out by applying the body fluid to a solid-phase immunoassay device, the level of CELSR1 in the sample may be indicated qualitatively by a calorimetric or fluorometric indicator, and the determining step may include comparing the indicator with a known standard.

In a related aspect, the invention includes a diagnostic device for use in screening for kidney cancer in a human subject, or staging treatment of kidney cancer in a subject. The device comprises (a) a structure for receiving a body-fluid sample from the subject, (b) an antibody specific against a selected domain or epitope of CELSR1, and associated with the structure and capable of reacting with body-fluid received in said structure, to produce, in combination with other reagents associated with the structure, a detectable reaction indicative of the level of CELSR1 in the sample, and (c) a known-standard indicator against which the level of detectable reaction produced can be assessed as an elevated level associated with kidney cancer.

The structure in the device may include a porous pad having the anti-CELSR1 binding protein embedded therein, for reaction with the fluid sample when the sample is applied to the pad, the detectable reaction may be indicated by a calorimetric or fluorimetric indicator, and the known standard indicator may include an indicia that represents a level of CELSR1 corresponding to that associated with kidney cancer.

The device may be employed in a kit which includes a spectrophotometic detector for generating a signal related to the level of CELSR1 produced, a microprocessor for comparing the signal with a know-standard signal value associated with kidney cancer, and a display for displaying an output of the microprocessor.

Also provided by the invention is a method of treating kidney cancer in a subject by the steps of (a) reacting a body-fluid sample from the subject with an antibody specific against a selected domain or epitope of CELSR1, (b) determining from the presence and/or amount of immunoassay product, whether the subject has a reduced level of CELSR1 protein lacking the specific domain or epitope, when compared with a normal range of CELSR1 in human samples, as an indicator of kidney cancer, and (c) if the subject has such a reduced CELSR1 level, administering a therapeutically effective amount of a CELSR1 binding agent effective, when bound to the surface of kidney cancer cells, to inhibit growth or viability of the cells. One exemplary antibody in the method is a human or humanized anti-CELSR1 antibody specific against an epitope contained within SEQ ID NO:1.

These and other aspects, objects, advantages, and features of the invention will become apparent to those persons skilled in the art upon reading the details of the invention as more fully described below.

DETAILED DESCRIPTION OF THE INVENTION

A. Definitions

The following terms have the definitions given below, unless otherwise indicated in the specification.

"Screening" for kidney cancer, in accordance with the present invention, means testing individuals for a level of CELSR1 that is indicative of kidney cancer or an elevated risk of kidney cancer.

"Staging" treatment of kidney cancer, in accordance with the present invention, involves determining the stage of kidney cancer in an individual, based on the level of CELSR1 detected, and tailoring the treatment to that stage. There are four recognized stages of kidney cancer, which are defined by the degree of localization of cancer cells. In addition, kidney cancer may be defined as early stage at which the cancer is responsive to a number of hormonal-based therapies, and a later, more serious androgen-independent stage.

"A reduced level of CELSR1 protein" may include, as an indicator of cancer, a reduced level of wildtype CELSR1 protein or a reduced level of CELSR1 protein having a specific epitope or domain. That is, either the absence of any CELSR1 protein or the presence of a defective CELSR1 protein may be indicative of cancer, e.g., kidney cancer.

B. CELSR1 Protein and Expression

Figure 1:
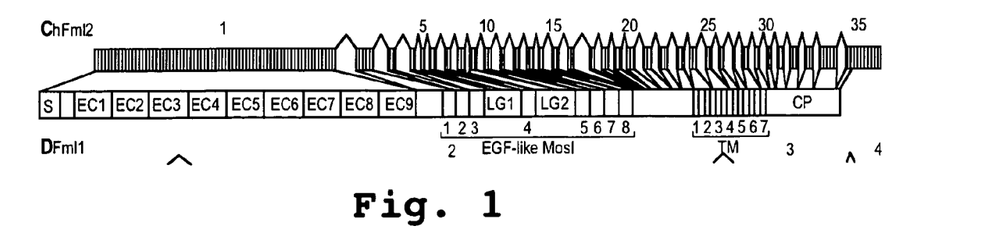
FIG. 1 shows the genomic organization of the human CELSR1 gene (a.k.a. flamingo 2) and a schematic representation of the protein it encodes.

The cadherin EGF LAG seven-pass G-type receptor-1 (CELSR1) protein[1-3], encoded by the CELSR1 gene (FIG. 1), is a member of the flamingo subfamily, which, in turn, is part of the cadherin superfamily. The flamingo subfamily consists of nonclassic-type cadherins, which do not interact with catenins. The flamingo cadherins are located at the plasma membrane and have at least eight cadherin domains, at least five calcium-binding epidermal growth factor-like (EGF_CA) domains, two laminin A G-type (LamG) domains, a laminin-type EGF-like (EGF_Lam) domain, and at least three receptor domains identified as (1) the HormR domain (a domain present in hormone receptors), (2) a GPS domain (G-protein-coupled receptor proteolytic site domain), and a 7 tm domain (7-transmembrane receptor domain from the secretin family). The amino acids sequences identified with these domains are given in the Sequence Listing below. It is believed that CELSR1 proteins are receptors mediating contact-mediated communication. The cadherin domains may act as homophilic binding regions, and the EGF-like domains may be involved in cell adhesion and receptor-ligand interactions.

The human unprocessed CELSR1 protein precursor has 3014 amino acid residues (AA) and a calculated molecular weight (MW) of 329486 Da; the mouse precursor has 3034 AA and a calculated MW of 330481 Da. The human gene contains 35 exons; all 9 protocadherin ectodomain repeats of the human protein are encoded by the large first exon[1]; in the mouse ortholog, this exon is split into exons 1 and 2. Part of the human exon 1, without all the other exons, is also transcribed in lung epithelial cells (EST CA944897), with a predicted protein of 188 AA.

The CELSR1 protein is expressed in the brain, where it is localized principally in the ependymal cell layer, choroid plexus and the area postrema; and in the spinal cord and in the eye. It is a developmentally regulated, neural-specific gene which plays an unspecified role in early embryogenesis. First detected at developmental stage E6 in the mouse, it is predominantly expressed in the developing central nervous system (CNS), the emerging dorsal root ganglia and cranial ganglia. In the CNS, expression is uniform along the rostrocaudal axis. During gastrulation, it is expressed in the vicinity of the primitive streak, and becomes predominant in that area at late gastrulation. At E10, it is detected in ventricular zones (VZ), but not in marginal zones (MZ), and weakly in other structures. Between E12 and E15, it is highly expressed in the VZ in all brain areas, but not in differentiated neuronal fields. In the newborn and postnatal stages, expression remains restricted to the VZ, but it is also weakly expressed in fetal lungs, kidney and epithelia[4].

C. Screening for CELSR1 -Related Cancers in Mice.

Cancer genes (oncogenes and tumor suppressor genes) were defined in a high throughput manner by using proviral tagging. Although viruses have not yet been implicated as a major cause of cancers in humans, research using tumor viruses has led to the discovery of many oncogenes and protooncogenes. In proviral tagging, mice are infected with a retrovirus that does not contain an oncogene (e.g., murine leukemia virus, MLV or murine mammary tumor virus, MMTV)[5-9]. Recently, the host range of this approach has been broadened by the use of a transposon[10, 11].

During retroviral infection, the virus integrates into the cellular genome and inserts its DNA near or within genes, which leads to various outcomes: (i) The insertion site is too far away from a protooncogene and thus does not activate it. In this case, there will be no selection for that cell. (ii) The provirus inserts within 200 kb of a protooncogene, but not within the gene (type 1). Here, either the viral promoter or the viral enhancer increases the expression level of the protooncogene. (iii) The provirus inserts within a gene, destroying or altering its function (type 2). There will be no selection for a cell that contains either type 1 or type 2 insertion events in a gene that is not a protooncogene or tumor suppressor gene. If integration results in the formation of a tumor, genes adjacent to the integration site can be identified, and classified as either protooncogenes or tumor suppressor genes. This method has been used to identify protooncogenes as well as to confirm already known protooncogenes discovered by virtue of their homology to viral oncogenes[5, 6, 8, 9, 12-15]. A tumor suppressor may be scored if a retrovirus lands within a gene and truncates or destroys it. In these cases, the suppressor may be haploinsufficient, or alternatively, the mutation on the other allele is provided spontaneously by the mouse. The integration event may also lead to more complex consequences, such as a dominant negative effect of the truncated gene product or the transcription of anti-sense or microRNA.

Figure 2:
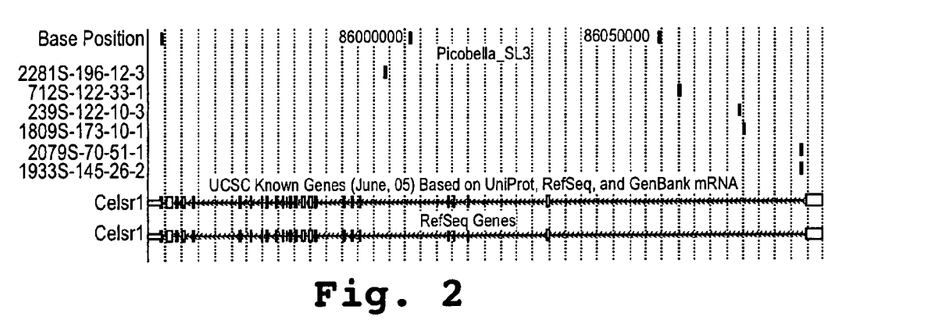
FIG. 2 shows the genomic organization of the mouse Celsr1 locus, as viewed by a customized screen print of the UCSC genome web site browser (March 2005 version of the mm6 gene assembly). Top, base position on chromosome 15. Vertical green bars represent the retroviral insertions into the locus in 6 independent tumors.

In a screen with T lymphotropic virus SL3-3, six independent tumors were recovered that contained proviral integrations in the mouse CELSR1 locus: five tumors contained integrations within intron 2 (which corresponds to human intron 1) while one tumor contained an integration within intron 6 (which corresponds to human intron 5) (FIG. 2). In the first five tumors, all 9 protocadherin ectodomain repeats are predicted to be separated from the rest of the protein. In tumor 6, the protocadherin domains plus part of the EGF-like motif are predicted to be separated from the rest of the protein. The results demonstrate that disruption of the cadherin and/or EGF-like domains in CELSR1 protein can trigger a tumor, and that therefore, tumors may be associated with CELSR1 proteins lacking a critical domain or epitope or with absence of the CELSR1 protein itself.

D. Expression of CELSR1 in Human Tumors and in Normal Tissue

Figure 3A:
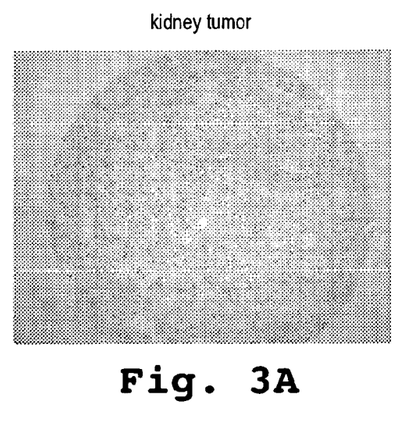
FIGS. 3A-3B shows an example of immunohistochemical stains of a human kidney tumor (renal cell carcinoma) (FIG. 3A), and matched normal kidney tissue (FIG. 3B) from the same patient. The polyclonal rabbit antibody used reacts to an epitope that is found between amino acid residues 90 and 150, which is encoded by exon 1.
Figure 3B:
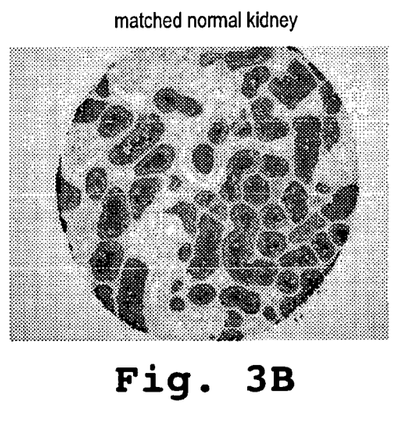

The mutations that were identified as causal in mouse tumor formation disrupted the gene after exon 2. In humans, exon 1 encompasses the sequences of both exons 1 and 2 of the mouse. In addition to the signal peptide, human exon 1 encodes the 9 cadherin domains of CELSR1. As the cadherin domains extend to AA 1197, a rabbit polyclonal antibody to an epitope that is included between AA 90 to 150 was used for the studies on oncogenic mutations that caused the (functional) loss of the ectodomains. Indeed, this domain was found to be missing in renal cell carcinomas (FIG. 3), whereas the normal counterpart of these tumor cells strongly expressed CELSR1 (FIG. 3). Clearly, the absence of part or all of the ectodomains is a marker for these tumors.

More generally, the invention provides a histological method for examining human kidney tissue for the presence and extent of cancer. In the method, kidney tissue is stained with a labeled antibody specific against a selected domain or epitope of CELSR1, e.g., fluorescence-labeled antibody (see Section E below), to attach the marker to the surface of tissue cells. The presence and extent of kidney cancer in the tissue is then determined based on a reduced distribution and extent of detectable marker with respect to the distribution and extent of marker in normal kidney cells.

E. Preparation of Anti-CELSR1 Antibody

This section describes production of anti-CELSR1 antibodies useful for diagnostic and therapeutic purposes, as described further in the sections below. The anti-CELSR1 antibody used in the present invention can be obtained by any a variety of conventional methods as a monoclonal, polyclonal, or recombinant antibody. One preferred antibody, particularly for diagnostic use, is a mouse monoclonal antibody, prepared according to well-known hybridoma methodology. Briefly, human CELSR1 may be first obtained, for example, by expressing the CELSR1 (MXR7) gene as disclosed by Lage, H. et al (Gene 188 (1997), 151-156). The purified CELSR1 protein acts as an immunogen. Alternatively, a partial peptide of CELSR1 can be used as a sensitization antigen. In particular, for generating antibodies specific against a selected epitope or domain of CELSR1, a peptide defining that domain or epitope may be used as the immunogen. These peptides can be defined by the sequences given in the Sequence Listing below. For example, to generate an antibody specific against an epitope contained in SEQ ID NO:1, the peptide defined by this sequence is employed as the immunogen.

Anti-CELSR1 antibodies useful in diagnostic applications may be labeled with a variety of detectable labels, including detectable reporters, such as enzymes for enzyme-linked immunosorbent assays (ELISA), detectable particles, such as gold particles and reporter-carrying liposomes, colorimetric or fluorescent reporters, labels such as quantum dot nanocrystal particles, radiolabels, and labels such as a biotin label by which secondary detectable labels, such as a reporter-labeled streptavidin label can be attached. In some assay formats, an unlabeled anti-CELSR1 antibody, for example, a mouse IgG antibody, is detected by reaction with a labeled antibody, e.g., a labeled anti-mouse IgG antibody.

For therapeutic uses, human monoclonal antibodies having binding activity to CELSR1, (see Japanese Patent Publication (Kokoku) No. 1-59878 B (1989)) can be produced by sensitizing in vitro human lymphocytes with CELSR1, and causing the sensitized lymphocytes to fuse with the human-derived myeloma cells having a permanent division potential. Alternatively, CELSR1 as an antigen can be administered to a transgenic animal having all the repertories of a human antibody gene to obtain anti-CELSR1 antibody-producing cells, and then human antibodies for CELSR1 may be obtained from the immortalized anti-CELSR1 antibody-producing cells (see International Patent Publication Nos. WO 94/25585, WO 93/12227, WO 92/03918 and WO 94/02602).

In still other methods, human or humanized antibodies specific against CELSR1 antigen can be prepared by recombinant technique, such as have been reported (see, for example, U.S. Pat. Nos. 6,090,382 and 6,258,562).

F. Diagnostic Methods and Reagents

In one aspect, the invention includes a method of screening for kidney cancer in a human subject, or staging treatment of kidney cancer in a subject. This is done, in accordance with the invention, by reacting a body-fluid sample from the subject with an antibody specific against a selected domain or epitope of CELSR1, and determining from the presence and/or amount of immunoassay product, whether the subject has a reduced level of CELSR1 protein lacking the specific domain or epitope, when compared with a normal range of CELSR1 in human samples, as an indicator of kidney cancer.

Preferred body-fluid samples are blood and urine. Where urine is assayed, the assayed level of CELSR1 indicative or kidney cancer is typically in the range less than about 0.1 ng/ml sample fluid.

The assay may be carried out by any of a variety of assay methods used for detecting body-fluid antigens, including ELISA techniques, homogeneous assays, for example, involving fluorescence quenching, and a variety of solid-phase sandwich assays in which the CELSR1 antigen is captured on by an anti-CELSR1 antibody carried on a solid support, and the immobilized antigen-antibody complex is labeled with a second anti-CELSR1 antibody, e.g., a second antibody carrying a calorimetric or gold-particle reporter.

Figure 4A:
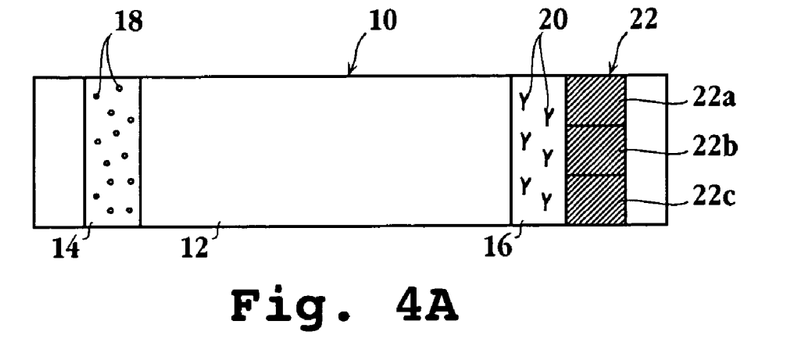
FIGS. 4A and 4B show a solid-phase diagnostic device for determining CELSR1 levels in a human patient, at initial (4A) and final stages (4B) of the assay.
Figure 4B:
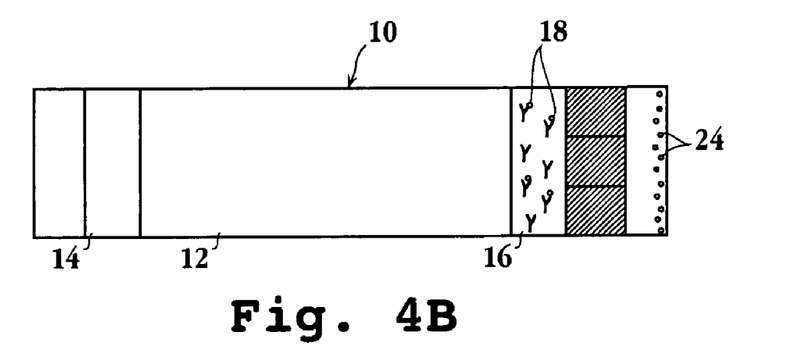

FIGS. 4A and 4B illustrate a solid-phase assay strip constructed in accordance with an embodiment of the invention, suitable for carrying out a sandwich immunoassay of the type just mentioned, and shown in initial and final assay states, respectively. The strip, indicated generally at 10, includes a porous support or pad 12 having a sample-application zone 14 in an upstream region of the support and a sample-detection zone 16 in a downstream region. The sample-application zone includes a detectable anti-CELSR1 antibody reagent, e.g., anti-CELSR1 antibodies labeled with gold particles, and carried in the zone in an unbound, i.e., non-immobilized form. This reagent is indicated by solid circles, such as at 18. Anti-CELSR1 antibodies, which may be the same or different from those in the labeled antibody reagent, are immobilized to the solid support within the detection zone, and are indicated by the "Y" shapes, such as at 20.

Also shown is a reference zone 22 which is located adjacent the detection zone and has one or more colored or shaded regions corresponding to different assay levels of CELSR1 in a body-fluid sample. In the embodiment shown, zone 22 includes three regions 22a, 22b, and 22c, corresponding to an assayed level of CELSR1 (a) below that associated with kidney cancer, (b) corresponding to a lower threshold level associated with kidney cancer, and (c) a level that is substantially higher, e.g., 2-3 times, higher than the threshold layer in region 22b, respectively. These three regions provide a known standard indicator against which the level of detectable reaction produced can be assessed as a level associated with kidney cancer. Together, the assay strip and reference zone constitute an assay device for use in screening for kidney cancer in a human subject, or for staging treatment of kidney in a human subject.

In operation, a known volume of a body-fluid sample to be tested is added to the sample-application zone of the strip, where it diffuses into the zone, allowing the antibody reagent to react with CELSR1 antigen in the sample to form an antigen-antibody complex. This complex and unbound antibody reagent then migrate downstream by capillarity toward the detection zone, where the antigen-antibody complex is captured by the immobilize antibody and the unbound reagent is carried to the end of the support, as indicated at 24. As can be appreciated, the higher the concentration of antigen in the body fluid, the higher the density of captured reagent in the detection zone and the greater the color or intensity in this zone. This color or intensity produced in the detection zone is compared with the standards in the reference zone to determine a qualitative level of CELSR1 associated with the presence or absence of kidney cancer. If a sub-threshold level or threshold level of CELSR1 is observed in the assay, the subject can be classified in a higher-probability category for the presence of cancer, and the subject may be recommended for additional testing and/or more frequent testing.

In another embodiment, the assay device includes an assay strip like that described above, but where the known-reference indicator is provided by a strip-reader instrument reader having (i) a reader slot for receiving the assay strip, (ii) a light source and an optical detection, e.g., a spectrophotometric detector, for detecting an assay-related optical condition at the detection zone of the assay strip, (iii) an electronics or processor unit which records and processes a signal from the optical detector, and converts the signal to an assayed level of CELSR1, and (iv) a user display screen or window. The instrument may report the actual CELSR1 body-fluid sample detected, allowing the operator to compare the displayed value with known standard indicator levels provided with the assay strip or instrument, to assess whether the subject has an reduced CELSR1 level associated with kidney cancer, or to assess the possible stage of the cancer, for purposes of treatment design. Alternatively, the instrument itself may contain stored known-standard indicator levels which can be compared internally with an assayed level to generate an output that indicates whether an reduced CELSR1 level associated with kidney cancer has been detected, or to indicate the stage of the cancer.

G. Identifying Genetic Mutation Associated with Kidney Cancer

In another aspect, the invention provides a method for identifying mutations associated with increased risk of kidney cancer in a human subject. In practicing the method, genomic DNA is extracted from human patients having kidney cancer, preferably including patients from men or women representing different racial and age groups. The DNA sequences that are examined, in particular, are (i) one or more of exons 1 to 35 of the CELSR1 on chromosome interval 22q13.3, including adjacent splice site acceptor and donor sequences of the exons, (ii) a 5' UTR region within 10 kB or less of exon 1 of the gene, and (iii) a 3'-UTR region within 10 kB or less of exon 35.

Mutations at one or more sites along the region are identified by comparing each of the sequences with sequences from the same region derived from normal (wildtype) kidney tissue. Preferably sequences from a number of wildtype individuals are determined to ensure a true wildtype sequence. For each extracted DNA, the patient and wildtype sequences are compared to identify mutations in the patient sequences, and thus mutations that are likely associated with increased risk of kidney cancer.

Once a large number of these mutations are identified, e.g., at least 50-200 or more, they may be used in constructing a genetic screening device, e.g., a gene chip, useful for screening individuals for genetic predisposition to kidney cancer. In one embodiment, the device includes a gene chip, such as shown at 30 in FIG. 5, having an array of regions, such as regions 34, 36, each containing bound known-sequence fragments, such as fragment 37 in region 34. The fragments or probes are preferably 25-70 bases in lengths, and each includes one of the above-identified mutations upstream of the CELSR1 gene that is associated with kidney cancer. In particular, the array sequences are designed in length and sequence to bind to those 22q13.3 mutations identified above, but not to associated fragments. Gene-chip construction, and detection of mutant sequences with such chips, are well known.

Figure 5:
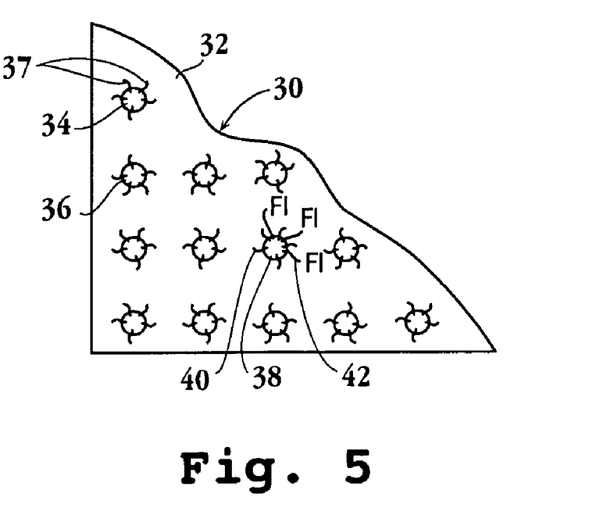
FIG. 5 shows a portion of a gene chip useful for diagnosing genetic predisposition to kidney cancer, constructed in accordance with the present invention.

In a typical genetic-screening procedure, patient cells are obtained, genomic DNA is extracted, and 22q1 3.3 sequence regions of interest are amplified by standard PCR, employing fluoresceinated probes. The amplified material is then reacted with the chip-array sequences, under suitable hybridization conditions, and the array surface is washed to remove unbound material, then scanned with a suitable chip reader to identify any mutated sequences associated with kidney cancer. The figure shows binding of a labeled genomic DNA fragment, indicated at 42, to an array region 38 having bound probe molecules 40. Detection of a fluorescent signal in this array region is diagnostic of a known genetic mutation in the critical upstream CELSR1 region of 22q13.3 interval and may be diagnostic of a genetic predisposition to kidney cancer.

In an alternative embodiment, the mutations identified as above are used to construct a set of molecular inversion probes (MIPs) capable of identifying the presence of genomic mutations. The construction and use of MIPs for identifying genetic mutations have been described (see, for example, Wang, et al., Nucleic acids research (England) 2005, Vol 33, p. 21.

H. Treatment Methods and Pharmaceutical Preparations

The invention also includes methods for treating, e.g., reducing the tumor burden in a human subject with kidney cancer. In one general immunotherapy approach, a patient diagnosed with kidney cancer is first confirmed as having reduced levels of CELSR1, according to assay methods described above. If the subject tests positive in this assay, he is treated by administration of anti-CELSR1 antibody. Preferably the antibody is a human or humanized antibody, prepared as described above, and is administered by IV or subcutaneous injection in a suitable physiological carrier. The antibody dose is preferably 1 to 10 mg/injection, and the patient is treated at intervals of every 14 days or so. During treatment, the patient is monitored for change in status of the cancer, typically by a combination of a tumor-visualization procedure and levels of kidney-related antigens, as above. The treatment may be carried out in combination with other kidney-cancer treatments, including drug or radio-isotope therapy, and may be continued until a desired diminution in tumor size is observed.

While the invention has been described with respect to particular embodiments and applications, it will be appreciated that various changes and modification may be made without departing from the invention as claimed.

Sequence Listing:

SEQ ID NO: 1: Antibody epitope sequence
(residues 90-150)
VRLVARSAPTALSRRLRARTHLPGCGARARLCGTGARLCGALCFPVPGG

CAAAQHSALAAP

SEQ ID NO: 2. Cadherin repeat domain 1
(residues 250-451)
YQVALFENEPAGTLILQLHAHYTIEGEEERVSYYMEGLFDERSRGYFRID

SATGAVSTDSVLDRETKETHVLRVKAVDYSTPPRSATTYITVLVKDTNDH

SPVFEQSEYRERVRENLEVGYEVLTIRASDRDSPINANLRYRVLGGAWDV

FQLNESSGVVSTRAVLDREEAAEYQLLVEANDQGRNPGPLSATATVYIEV

ED

SEQ ID NO:3. Cadherin repeat domain 2
(residues 357-557)
EYRERVRENLEVGYEVLTIRASDRDSPINANLRYRVLGGAWDVFQLNESS

GVVSTRAVLDREEAAEYQLLVEANDQGRNPGPLSATATVYIEVEDENDNY

PQFSEQNYVVQVPEDVGLNTAVLRVQATDRDQGQNAAIHYSILSGNVAGQ

FYLHSLSGILDVINPLDFEDVQKYSLSIKAQDGGRPPLINSSGVVSVQVL

D

SEQ ID NO: 4. Cadherin repeat domain 3
(residues 464-663)
YVVQVPEDVGLNTAVLRVQATDRDQGQNAAIHYSILSGNVAGQFYLHSLS

GILDVINPLDFEDVQKYSLSIKAQDGGRPPLINSSGVVSVQVLDVNDNEP

IFVSSPFQATVLENVPLGYPVVHIQAVDADSGENARLHYRLVDTASTFLG

GGSAGPKNPAPTPDFPFQIHNSSGWITVCAELDREEVEHYSFGVEAVDHG

-continued

SEQ ID NO:5. Cadherin repeat domain 4
(residues 569-781)
PFQATVLENVPLGYPVVHIQAVDADSGENARLHYRLVDTASTFLGGGSAGP

KNPAPTPDFPFQIHNSSGWITVCAELDREEVEHYSFGVEAVDHGSPPMSS

STSVSITVLDVNDNDPVFTQPTYELRLNEDAAVGSSVLTLQARDRDANSV

ITYQLTGGNTRNRFALSSQRGGGLITLALPLDYKQEQQYVLAVTASDGTR

SHTAHVLINVTD

SEQ ID NO: 6. Cadherin repeat domain 5
(residues 691-884)
TYELRLNEDAAVGSSVLTLQARDRDANSVITYQLTGGNTRNRFALSSQRG

GGLITLALPLDYKQEQQYVLAVTASDGTRSHTAHVLINVTDANTHRPVFQ

SSHYTVSVSEDRPVGTSIATLSANDEDTGENARITYVIQDPVPQFRIDPD

SGTMYTMMELDYENQVAYTLTIMAQDNGIPQKSDTTTLEILILD

SEQ ID NO: 7. Cadherin repeat domain 6
(residues 793-991)
HYTVSVSEDRPVGTSIATLSANDEDTGENARITYVIQDPVPQFRIDPDSG

TMYTMMELDYENQVAYTLTIMAQDNGIPQKSDTTTLEILILDANDNAPQF

LWDFYQGSIFEDAPPSTSILQVSATDRDSGPNGRLLYTFQGGDDGDGDFY

IEPTSGVIRTQRRLDRENVAVYNLWALAVDRGSPTPLSASVEIQVTILD

SEQ ID NO: 8. Cadherin repeat domain 7
(residues 896-1093)
FYQGSIFEDAPPSTSILQVSATDRDSGPNGRLLYTFQGGDDGDGDFYIEP

TSGVIRTQRRLDRENVAVYNLWALAVDRGSPTPLSASVEIQVTILDINDN

APMFEKDELELFVEENNPVGSVVAKIRANDPDEGPNAQIMYQIVEGDMRH

FFQLDLLNGDLRAMVELDFEVRREYVLVVQATSAPLVSRATVHILLVD

SEQ ID NO: 9. Cadherin repeat domain 8
(residues 1003-1197)
ELELFVEENNPVGSVVAKIRANDPDEGPNAQIMYQIVEGDMRHFFQLDLL

NGDLRAMVELDFEVRREYVLVVQATSAPLVSRATVHILLVDQNDNPPVLP

DFQILFNNYVTNKSNSFPTGVIGCIPAHDPDVSDSLNYTFVQGNELRLLL

LDPATGELQLSRDLDNNRPLEALMEVSVSDGIHSVTAFCTLRVTI

SEQ ID NO: 10. EGF_CA domain 1 (calcium-
binding EGF-like domain, present in a large number
of membrane-bound and extracellular (mostly
animal) proteins) (residues 1363-1399)
EIDLCYSDPCGANGRCRSREGGYTCECFEDFTGEHCE SEQ ID NO: 11. EGF_CA domain 2
(residues 1407-1441)
CANGVCKNGGTCVNLLIGGFHCVCPPGEYERPYCE SEQ ID NO: 12. LamG domain 1 (Laminin G)
(residues 1444-1627)
TRSFPPQSFVTFRGLRQRFHFTISLTFATQERNGLLLYNGRFNEKHDFIA

LEIVDEQVQLTFSAGETTTTVAPKVPSGVSDGRWHSVQVQYYNKPNIGHL

GLPHGPSGEKMAVVTVDDCDTTMAVRFGKDIGNYSCAAQGTQTGSKKSLD

LTGPLLLGGVPNLPEDFPVHNRQFVGCMRNLSVD

SEQ ID NO: 13. EGF_CA domain 3
(residues 1651-1685)
NFCDGRRCQNGGTCVNRWNMYLCECPLRFGGKNCE SEQ ID NO: 14. LamG domain 2 (residues 1694-1846)
FSGESVVSWSDLNIIISVPWYLGLMFRTRKEDSVLMEATSGGPTSFRLQI

LNNYLQFEVSHGPSDVESVMLSGLRVTDGEWHHLLIELKNVKEDSEMKHL

VTMTLDYGMDQNKADIGGMLPGLTVRSVVVGGASEDKVSVRRGFRGCMQG

VRM

SEQ ID NO: 15. EGF_CA domain 4
(residues 1871-1908)
DVDDPCTSSPCPPNSRCHDAWEDYSCVCDKGYLGINCV SEQ ID NO: 16. EGF_CA domain 5
(residues 1908-1946)
VDACHLNPCENMGACVRSPGSPQGYVCECGPSHYGPYCE SEQ ID NO: 17. EGF_Lam domain (Laminin-
type epidermal growth factor-like domain)
(residues 2002-2040)
PCDCFPHGSHSRTCDMATGQCACKPGVIGRQCNRCDNPF SEQ ID NO: 18. HormR domain (domain present in
hormone receptors) (residues 2052-2113)
YNGCPKAFEAGIWWPQTKFGQPAAVPCPKGSVGNAVRHCSGEKGWLPPEL

FNCTTISFVDLR

SEQ ID NO: 19. GPS (G-protein-coupled receptor
proteolytic site domain) (residues 2407-2460)
TKPVCVFWNHSLAVGGTGGWSARGCELLSRNRTHVACQCSHTASFAVLMD

ISRR

SEQ ID NO: 20. 7tm (7 transmembrane receptor
(Secretin family)) (residues 2465-2708)
VLPLKIVTYAAVSLSLAALLVAFVLLSLVRMLRSNLHSIHKHLAVALFLS

QLVFVIGINQTENPFLCTVVAILLHYIYMSTFAWTLVESLHVYRMLTEVR

NIDTGPMRFYYVVGWGIPAIVTGLAVGLDPQGYGNPDFCWLSLQDTLIWS

FAGPIGAVIIINTVTSVLSAKVSCQRKHHYYGKKGIVSLLRTAFLLLLLI

SATWLLGLLAVNRDALSFHYLFAIFSGLQGPFVLLFHCVLNQEV

The invention claimed is:

1. A histological method for examining human kidney tissue for the presence of kidney cancer, comprising
   staining the kidney tissue with an antibody specific against a selected domain or epitope of CELSR1 and labeled with a detectable marker, to attach the marker to the surface of tissue cells having surface bound CELSR1 protein with that epitope or domain, and
   determining, based on a reduced distribution and extent of detectable marker with respect to the distribution and extent of marker in normal kidney cells, the presence of kidney cancer in the tissue.

2. The method of claim 1, wherein the antibody is specific against an epitope contained within SEQ ID NO:1.

3. The method of claim 1, wherein the antibody is specific against an extracellular domain selected from the group consisting of (i) a cadherin domain, (ii) an EGF_CA domain, (iii) a LamG domain, (iv) an EGF_Lam domain.

4. The method of claim 3, wherein the antibody is specific against a cadherin domain selected from the group consisting of SEQ ID NOS: 2-9.

5. The method of claim 3, wherein the antibody is specific against an EGF_CA domain selected from the group consisting of SEQ ID NOS: 10, 11, 13, 15, and 16.

6. The method of claim 3, wherein the antibody is specific against a LamG domain selected from the group consisting of SEQ ID NOS: 12 and 14.

7. The method of claim 3, wherein the antibody is specific against an EGF Lam domain defined by SEQ ID NO: 17.

8. The method of claim 3, wherein the antibody is specific against a receptor site selected from the group consisting of SEQ ID NOS: 18-20.

* * * * *